US006947585B1

(12) United States Patent
Jones

(10) Patent No.: US 6,947,585 B1
(45) Date of Patent: Sep. 20, 2005

(54) ON-LINE CORRECTION OF PATIENT MOTION IN THREE-DIMENSIONAL POSITRON EMISSION TOMOGRAPHY

(75) Inventor: William F. Jones, Knoxville, TN (US)

(73) Assignee: CTI PET Systems, Inc., Knoxville, TN (US)

( * ) Notice: Subject to any disclaimer, the term of this patent is extended or adjusted under 35 U.S.C. 154(b) by 563 days.

(21) Appl. No.: 09/649,499

(22) Filed: Aug. 28, 2000

(51) Int. Cl.[7] ............................................... G06K 9/00
(52) U.S. Cl. ..................... 382/131; 250/363.04; 378/4; 378/21
(58) Field of Search ............................... 382/131, 260, 382/128; 378/901, 21, 4; 250/363.04

(56) References Cited

U.S. PATENT DOCUMENTS

| | | | | |
|---|---|---|---|---|
| 4,583,241 | A | * | 4/1986 | Walters ........................ 378/19 |
| 4,887,211 | A | * | 12/1989 | Thiel et al. .................. 382/131 |
| 4,937,848 | A | * | 6/1990 | Horbaschek et al. ....... 378/98.2 |
| 5,224,037 | A | * | 6/1993 | Jones et al. ................. 382/131 |
| 5,565,684 | A | * | 10/1996 | Gullberg et al. ....... 250/363.04 |
| 6,556,720 | B1 | * | 4/2003 | Avinash ....................... 382/260 |
| 6,865,247 | B2 | * | 3/2005 | Hagiwara ....................... 378/4 |

OTHER PUBLICATIONS

B.J. Lopresti, et al.—Implementation and Performance of an Optical Motion Tracking System for High Resolution Brain Pet Imaging, *IEEE Transactions On Nuclear Science*, vol. 46 No. 6, Dec. 1999.
Don Murray, et al.—Motion Tracking with an Active Camera, *IEEE Transactions on Pattern Analysis and Machine Intelligence*, vol. 16, No. 5, May 1994.
Michael V. Green, et al.—Head Movement in Normal Subjects During Simulated PET Brain Imaging with and without Head Restraint, *The Journal Of Nuclear Medicine*, vol. 35 No. 9, Sep. 1994.
Y. Picard, et al.—Digitized Video Subject Positioning and Surveillance System for PET, *IEEE Transactions on Nuclear Science*, vol. 42, No. 4, Aug. 1995.
Seth R. Goldstein, et al.—A Head Motion Measurement System Suitable for Emission Computed Tomography, *IEEE Transactions on Medical Imaging*, vol. 16, No. 1, Feb. 1997.
Antonio Russo, Development of a Motion Tracking System for Position Tomography, Diploma thesis at Micro-Engineering Department of PET Facility, University of Pittsburgh.

* cited by examiner

*Primary Examiner*—Jose L. Couso
*Assistant Examiner*—Tom Y. Lu
(74) *Attorney, Agent, or Firm*—Pitts & Brittian, PC

(57) ABSTRACT

A device and method for on-line correction of patient motion in three-dimensional positron emission tomography. The devices encompass an on-line hardware pipelining architecture to support 3D translation, normalization, and weighted histogramming as required. For the 3D translation circuit, a first digital pipeline latch is provided for receiving data as it is collected by the PET scanner. A bank of multiplier circuits receives the PET scan data. Each multiplier circuit receives and multiplies a portion of the entire scan data simultaneous with each other multiplier circuit. The product of each multiplier circuit is output to a second digital pipeline latch. The data is then passed to a bank of adders, each of which supports four input variables. While a specific LOR and a current object orientation are input to the first digital pipeline latch, processing for a different LOR and an earlier object orientation are stored in the second digital pipeline latch. Additionally, fully transformed coordinates from a third LOR are loaded into a third digital pipeline latch. As the banks may each complete their respective tasks under a threshold time limit, the pipelining technique permits the entire 3D transformation for the AB pair to take place in real time. Further, on-line normalization and on-line weighted histogramming are also performed in real time.

7 Claims, 3 Drawing Sheets

ON-LINE CORRECTION OF PATIENT MOTION IN THREE-DIMENSIONAL POSITRON EMISSION TOMOGRAPHY

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

1. Field of Invention

This invention relates to the field of positron emission tomography (PET). More specifically, the present invention is related to a device and method for improving PET resolution through on-line correction of patient motion.

2. Description of the Related Art

In the art of PET detection, it is known that the resolution of a scan is in part dependent upon the amount of motion of the patient during the scan, and specifically the motion of the portion of the body being scanned. It is known that typical PET scans last from fifteen (15) minutes to three (3) hours. Ideally, if the patient could lie motionless during a PET scan, a high resolution PET system such as the CTI Pet Systems, Inc., EXACT HR+ is capable of 4 to 5 mm 3-D image resolution. However, if the patient or object in the field of view (FOV) does not remain stationary, the PET image is blurred. Practically speaking, inadvertent or disease-induced patient motion over the course of the scan currently blurs the 4 to 5 mm resolution to a far less effective 10 to 15 mm or worse.

Recent work has shown that techniques exist for tracking patient motion during the PET scan. B. J. Lopresti et al., *Implementation and Performance of an Optical Motion Tracking System for High Resolution Brain PET Imaging*, IEEE Transactions on Nuclear Science, Vol. 46, No. 6, 2059–2067 (December 1999), shows effective tracking of patient head motion to all 6 degrees of 3-D movement. Specifically, they show tracking of the X-, Y-, and Z-offsets to an accuracy of fractions of a millimeter, as well as yaw, pitch, and roll to acceptable angular accuracy. Encouraged by Lopresti's effort, the industry is currently moving toward both partial and more complete analytical solutions to the blurring problem. Partial solutions include gating the PET data into time slices during which the patient is shown to be more stationary. In more complete solutions the measured head position is applied to small time slice groups of PET data or even to individual detector-pair event PET data. These solutions each apply a correction for patient motion after the PET scan has completed. The most likely application of the more complete correction is a list mode approach in which all the raw PET data is collected in a computer disk file. After the PET scan completes the data is reprocessed. While this event-by-event list mode approach corrects for the motion of, for example, a patient's head, the reprocessing of the file data is a time consuming task.

In clinical PET applications, economic pressures demand high patient throughput without compromise to ease of use. The aforementioned list mode approach to motion de-blurring is problematic in view of these economic pressures in that more operator interaction and unacceptably long processing times are required. Either the data that is stored for reprocessing must be moved to a separate processor, or the data is reprocessed on the computer used for scanning. For a typical scan of 30–45 minute duration, reprocessing the data requires 30 minutes to 3 hours of scanner time (equivalent to approximately one to six additional scans) or an independent computing system. Taking this further, if the PET scanner is to be used almost continuously for scanning only, it will be seen that several independent computing systems are required to reprocess the data collected in a most time-efficient manner.

Typically, with respect to PET, the skull and brain are considered a single, rigid object. However, whole body PET scans also suffer from a lack of correction for motion. While problems limit effectiveness compared to brain scans, gross motions of the whole human body may also be de-blurred. PET cardiac gating is one example of a well-known but crude method to compensate for the motion of the heart during a PET scan. Difficult technical challenges remain to more effectively correct for the relative motions between and within individual organs such as, among others, the heart, lungs, liver, and lymph nodes.

Another known obstacle to on-line motion correction in the context of most existing PET applications is on-line normalization. In standard PET, on-line histogramming permits an accumulating tally of true events to be recorded in computer memory bins. One bin is typically reserved for each line of response (LOR) or small group of LORs. Histogramming adds or subtracts unity to a designated memory bin for each prompt or delayed event. Normalization serves to compensate for variations in detector pair efficiency by scaling the bin values. This scaling is typically applied after histogramming completes and is almost never applied in any on-line or real-time fashion. To apply normalization in real time for typical human PET requires somewhat more complex electronic systems than are in typical use today. These on-line systems must rapidly add or subtract scalar values instead of unity.

Mathematical techniques for transformation from one 3-D coordinate system to another are well known. In Schaum's *Mathematical Handbook* are listed equations for translation and rotation from one 3-D coordinate system (x, y, z) to another (x', y', z'). Representative equations are as follows:

$$x' = d_{xx}*x + d_{xy}*y + d_{xz}*z + X \qquad (1)$$

$$y' = d_{yx}*x + d_{yy}*y + d_{yz}*z + Y \qquad (2)$$

$$z' = d_{zx}*x + d_{zy}*y + d_{zz}*z + Z \qquad (3)$$

where:
   X, Y, and Z are translational offsets from the coordinate system (x, y, z) to the coordinate system (x', y', z');
   $d_{xx}$, $d_{xy}$, and $d_{xz}$ are direction cosines between the x-, y-, and z-axes and the x' axis, respectively;
   $d_{yx}$, $d_{yy}$, and $d_{yz}$ are direction cosines between the x-, y-, and z-axes and the y' axis, respectively; and
   $d_{zx}$, $d_{zy}$, and $d_{zz}$ are direction cosines between the x-, y-, and z-axes and the z' axis, respectively.

These three equations require nine multiplication operations and three operations involving the addition of four input variables.

The known digital electronic technique of pipelining is applied to arithmetic operations such that the speed of the electrical circuit is limited not by the whole computation but instead by the slowest individual piece of the computation. See *Introduction to Computer Architecture* by H. S. Stone, 1975, page 386, Section 9.3, "Pipelining as a Design Principle". However, such technique has not been shown in the prior art to be successful in the environment of on-line correction of patient data in a PET scan to account for patient motion.

Therefore, it is an object of the present invention to employ pipelining to reduce the throughput time of patient data to allow for on-line, real time correction for patient motion in a PET scan.

Further, it is an object of the present invention to provide a device whereby as each PET coincidence event is detected, each line of response (LOR) is re-mapped or rebinned in real time from a stationary 3-D reference space of the PET detector array into a virtual 3-D reference space which moves dynamically with the patient.

BRIEF SUMMARY OF THE INVENTION

Other objects and advantages will be accomplished by the present invention which serves to apply a correction for patient motion in an on-line and real-time manner. The present invention further provides a means whereby as each PET coincidence event is detected, each line of response (LOR) is re-mapped or rebinned in real time from a stationary 3-D reference space of the PET detector array into a virtual 3-D reference space which moves dynamically with the patient. On-line normalization is also applicable to properly histogram events which are corrected for patient movement.

The present invention incorporates a core hardware pipelining architecture to perform the transformation between 3-D coordinate spaces as required. A first digital pipeline latch is provided for receiving coincidence event and patient position data as it is collected by the PET scanner. A bank of multiplier circuits receives the PET scan data. Each multiplier circuit receives and multiplies a respective portion of each data set simultaneous with each of the other multiplier circuits. The product of each multiplier circuit is output to a second digital pipeline latch. The data is then passed to a bank of adders, each of which supports four input variables.

While data for a specific LOR and a current object orientation are input to the first digital pipeline latch, processing for a different LOR and an earlier object orientation (limited to the 3 translation offsets, X Y Z) are stored in the second digital pipeline latch. Additionally, fully transformed coordinates from a third LOR are loaded into a third digital pipeline latch. As the banks may each complete their respective tasks under a threshold time limit, the pipelining technique permits the entire 3-D transformation for the "AB" gamma coincidence detector pair to take place in real time.

In event-by-event normalization, a scalar value typically in the range of 0.01 to 100 is added to (or subtracted from) the indicated projection space bin value for each LOR prompt (or delayed). For on-line correction of object motion, the normalization is applied in an on-line fashion. The result of on-line normalization is that the final total projection bin values are scaled to properly correct for variations in detector efficiency and dead-time.

BRIEF DESCRIPTION OF THE DRAWING

The above mentioned features of the invention will become more clearly understood from the following detailed description of the invention read together with the drawing in which.

DETAILED DESCRIPTION OF THE INVENTION

Figure 1:
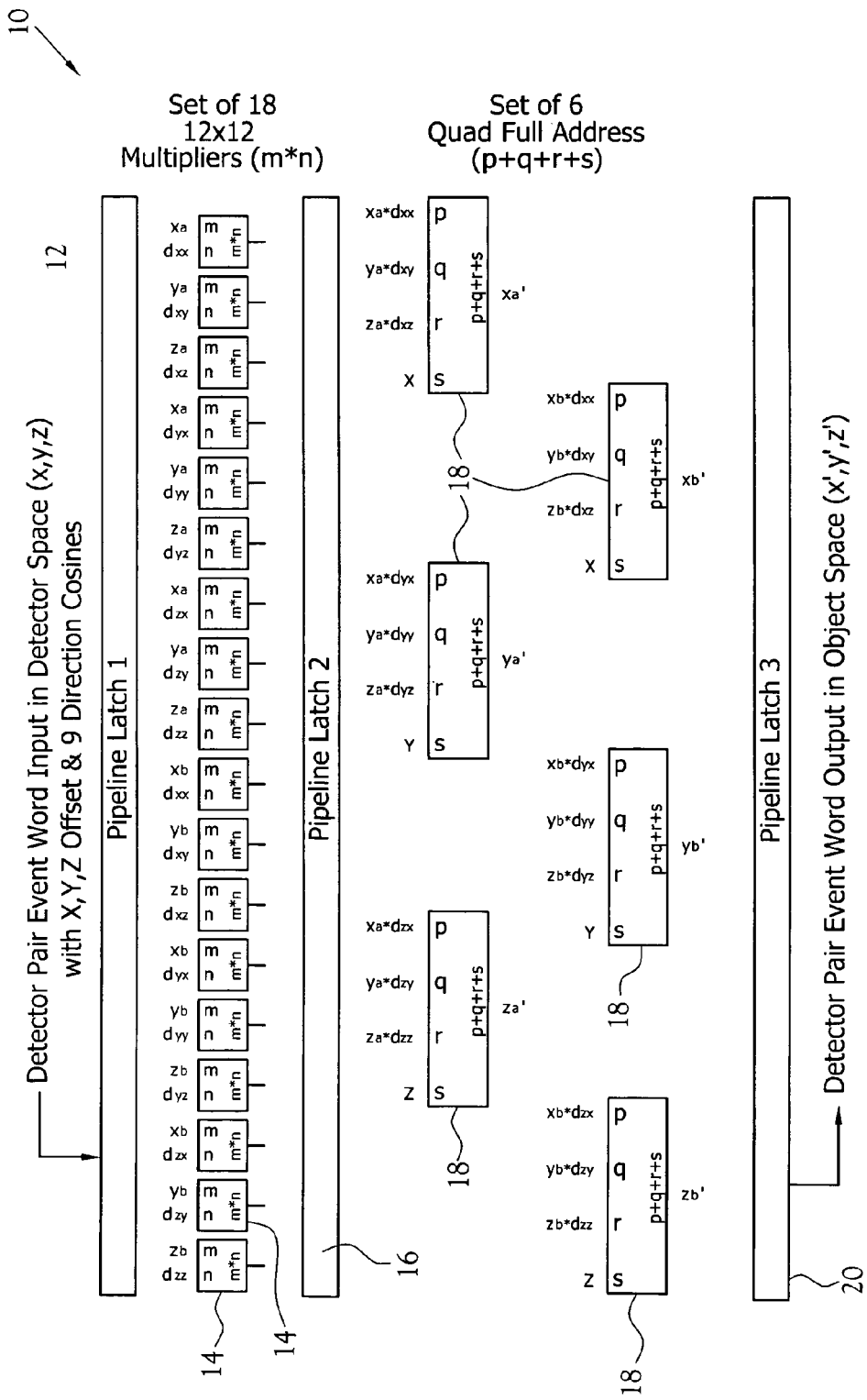
FIG. 1 is a schematic of the core hardware pipelining architecture for performing on-line correction of patient motion in three-dimensional positron emission tomography.

A device and method for on-line correction of patient motion in three-dimensional positron emission tomography (3D PET) incorporating various features of the present invention is illustrated generally at 10 in the figures. The device for on-line correction of patient motion in 3D PET, or device 10, is designed to apply a correction for patient motion in an on-line and real-time manner. Moreover, the device 10 provides a means whereby as each PET coincidence event is detected, each line of response (LOR) is re-mapped or rebinned in real time from a stationary 3-D reference space of the PET detector array into a virtual 3-D reference space which moves dynamically with the patient.

Discussion of the present invention will be directed primarily toward correction of motion of the patient's head. However, it will be understood the present invention is applicable to other portions of a patient's body as well. As discussed previously, with respect to PET, the skull and brain are typically considered a single, rigid object. Accordingly, correction for subtle patient head motion is effective for typical PET operation. However, whole body PET scans also suffer from a lack of correction for motion. Accordingly, it is within the scope of the present invention to track and correct for the gross motions of the human as a single rigid object or as a collection of rigid objects. For example, it is foreseeable by one skilled in the art that the present invention, if replicated within each PET device, be used to differentially track the upper chest and hips as two separate rigid bodies. Similarly, the present invention may be used to simultaneously track the head, upper chest, hips, upper arm, lower leg, etc.

For correction of single rigid body motion in PET, two coordinate spaces are defined. A detector space (x, y, z) represents the coordinates fixed in relation to the 3-D array of PET detectors. An object space (x', y', z') represents the virtual 3-D coordinates fixed in relation to an object in the FOV. For illustrative purposes of the present invention, the object in the FOV is the patient's head. For any given PET coincidence event, a pair of crystal locations given in x-, y-, z-coordinates represents a detector-pair LOR. The first, or "A", crystal of a coincidence pair "AB" is referenced as residing in the unique detector location $(x_a, y_a, z_a)$. The second, or "B" crystal is referenced as residing in detector location $(x_b, y_b,$ and $z_b)$.

At the beginning of the scan the object 3-D coordinate space is arbitrarily defined to be the same as that defined for the detector space. Specifically, the nine values X, Y, Z, $d_{xy}$, $d_{xz}$, $d_{yx}$, $d_{yz}$, $d_{zx}$, and $d_{zy}$ from Eqs. 1–3 are all zero and the values $d_{xx}$, $d_{yy}$, and $d_{zz}$ are all unity. As the scan progresses and object motion occurs, the translation offsets and direction cosine values vary. In order to correct for the motion of the object relative to the detector array, object coordinates are calculated for the two crystal locations in real time. The "A" detector location in object space is $(x_a', y_a', z_a')$. The "B" location in object space is $(x_b', y_b', z_b')$. The transformation equations, Eqs. 1–3 listed above, are applied both for the "A" detector position and the "B" detector position.

Transformation of "A" detector location from detector space to object space is as follows:

$$x_a' = d_{xx}*x_a + d_{xy}*y_a + d_{xz}*z_a + X \quad (1a)$$

$$y_a' = d_{yx}*x_a + d_{yy}*y_a + d_{yz}*z_a + Y \quad (2a)$$

$$z_a' = d_{zx}*x_a + d_{zy}*y_a + d_{zz}*z_a + Z \quad (3a)$$

Likewise, transformation of "B" detector location from detector space to object space is as follows:

$$x_b' = d_{xx}*x_b + d_{xy}*y_b + d_{xz}*z_b + X \quad (1b)$$

$$y_b' = d_{yx}*x_b + d_{yy}*y_b + d_{yz}*z_b + Y \quad (2b)$$

$$z_b' = d_{zx}*x_b + d_{zy}*y_b + d_{zz}*z_b + Z \quad (3b)$$

As current state-of-the-art PET systems detect and generate up to twelve million AB pairs per second, the task is to calculate these 2 transformation equation sets every 83 nanoseconds.

Illustrated in FIG. 1 is a diagram of the 3-D transformation hardware pipelining architecture 10 of the present invention. A first digital pipeline latch 12 is provided for receiving data as it is collected by the PET scanner. A bank of multiplier circuits 14 receives the PET scan data. Each multiplier circuit 14 receives and multiplies a respective portion of the current LOR and positional data set simultaneously with each of the other multiplier circuits 14. Thus, the multiplier circuits 14 collectively function simultaneously. In the preferred embodiment, each multiplier circuit 14 performs its computation in no more than 83 ns. Illustrated are 18 multiplier circuits 14 for providing 18 integers. The product of each multiplier circuit 14 is output to a second digital pipeline latch 16. Also, the X, Y & Z translational offset variables are passed from the first latch 12 to the second 16. From the second latch 16, the data set is then passed to a bank of adders 18, each of which supports four input variables. Each input variable consists of at least twelve bits. Illustrated are six adders 18. The adders 18 also operate simultaneously and in less than 83 ns.

While a specific LOR and a current object orientation are input to the first digital pipeline latch 12, processing for a different LOR and an earlier object X, Y and Z offset are stored in the second digital pipeline latch 16. Additionally and simultaneously, fully transformed ($x_a'$, $y_a'$, $z_a'$, $x_b'$, $y_b'$, $z_b'$) coordinates from a third LOR are loaded into a third digital pipeline latch 20. As the banks shown may each complete their respective tasks in 83 ns or less, the pipelining technique permits the entire 3-D transformation for the AB pair to take place on a sustained basis of twelve million events per second.

In addition to on-line 3-D coordinate transformation, on-line normalization is required for effective motion correction in PET. In typical PET practice, normalization is required and applied after histogramming. For this normalization, a scalar value, typically in the range of 0.001 to 100, is determined and applied to the already histogrammed projection bin data. These scalar values are determined to correct for various points of detector nonuniformity. These points of nonuniformity include variations in detector-to-detector sensitivity, dead-time losses, and the like. In some PET systems, an array of scalar values is produced and maps one-to-one with the array of projection bins. Here each final value in the scalar array is computed as the product of individual normalization correction values. Other PET systems, taking advantage of inherent patterns of uniformity and predictability, may effectively apply normalization correction by processing a much smaller array of normalizing scalar values. For example, PET tomographs which rotate have very uniform sensitivity among the groups of projection bins with equal radial distance from the FOV center. Also, PET tomographs which employ continuous bed motion enjoy very uniform sensitivity from projection bin to projection bin along the FOV axis. This uniformity comes as a result of each and every FOV plane being serviced by each and every tomographic projection bin. In addition, predictable patterns of detector sensitivity exist across the transaxial extent of the FOV. Such patterns of detector sensitivity allow a small list of scalar values to correct for this variation among a very large number of projection bins. In the present invention, the final scalar values are computed as the product of these various normalization component values.

In typical PET practice, each composite scalar value is simply applied as a multiplication to the respective bin values and only the resulting products of bin values and scalar values are used for further data processing, such as for image reconstruction. In contrast, on-line normalization must be applied as a part of a "weighted" histogramming process. For systems employing weighted histogramming with on-line normalization, histogramming no longer consists of the addition or subtraction of unity to/from respective projection bins. Instead, weighted histogramming with on-line normalization consists of the addition or subtraction of scalar integer values.

Figure 2:
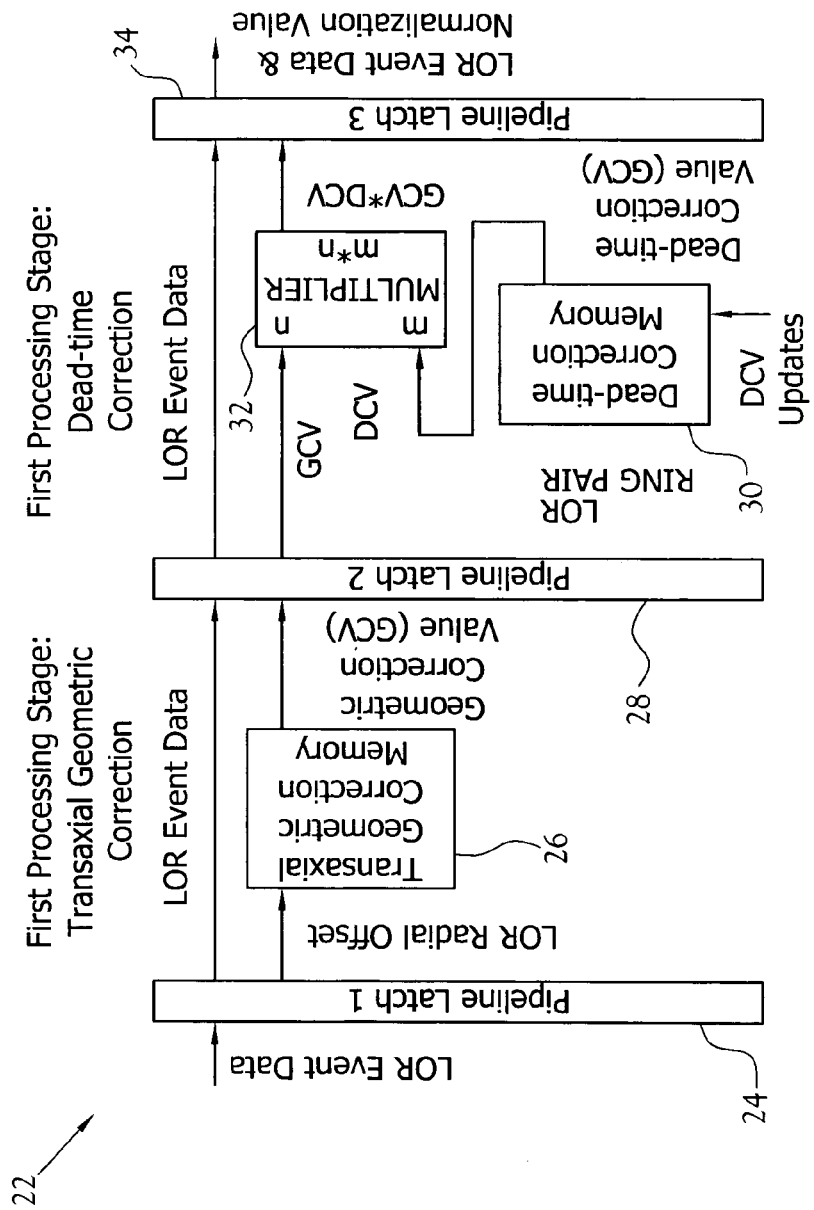
FIG. 2 illustrates a schematic representation of an example on-line computation of the composite normalization scalar value.
Figure 3:
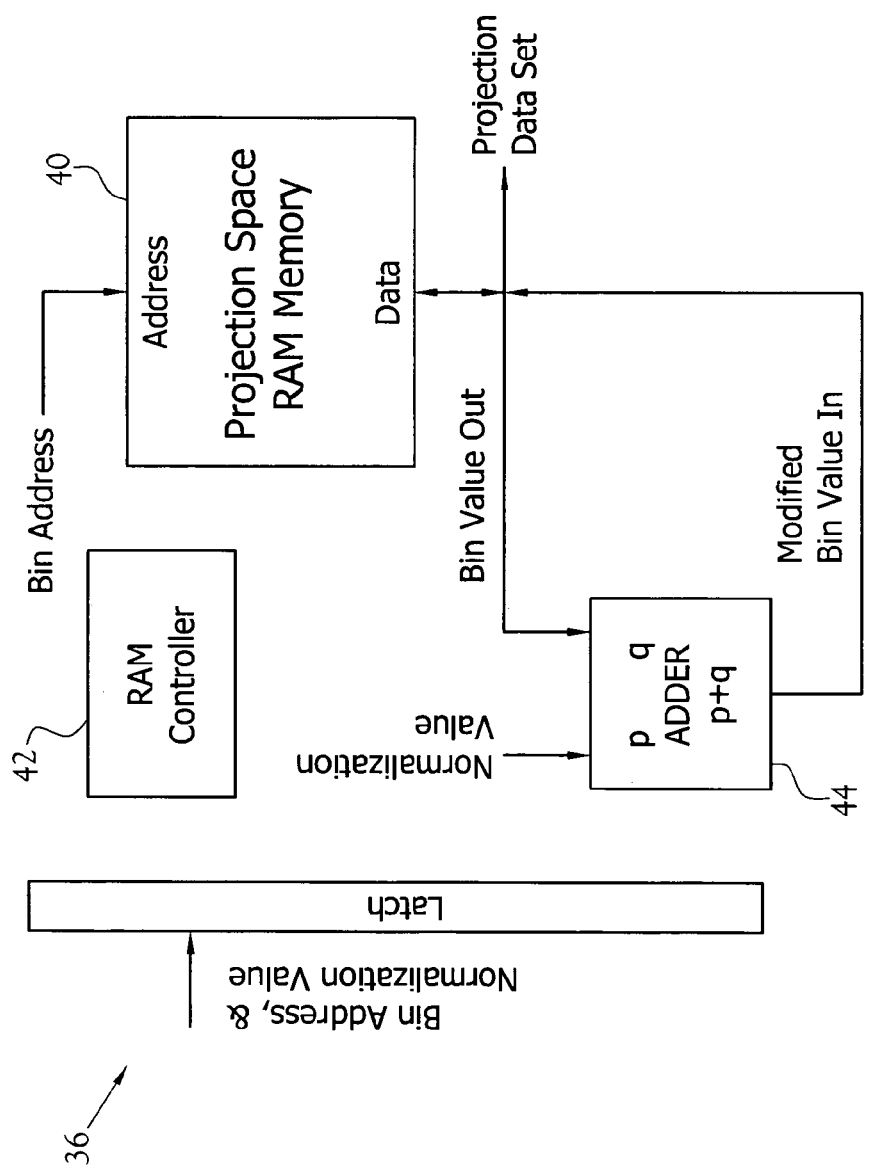
FIG. 3 illustrates a schematic representation for on-line weighted histogramming.

In addition to the 3-D transformation hardware circuit described in FIG. 1, FIGS. 2 and 3 illustrate circuits which support weighted histogramming with on-line normalization. FIG. 2 illustrates a schematic representation of an example of on-line computation of the composite normalizing scalar value. Three digital pipeline stages are shown supporting two processing stages. Prior to 3-D translation, LOR event data in the form of detector index pairs is input into the first pipeline latch 24. The first processing stage shown serves to provide a transaxial geometric correction value for each event processed. A simple memory circuit 26 serves as a look-up table to provide, within the maximum threshold time (e.g., 83 ns) the indicated integer geometric correction value (GCV) for this event. This correction value is passed on to the second pipeline latch 28 with the remainder of the LOR event information. In the second processing stage, memory circuit 30 also serves as a look-up table. The memory circuit 30 is updated periodically to represent current integer dead time correction values (DCV). The memory 30 is indexed on a coincidence ring basis to provide the indicated DCV for each event. In addition, the second processing stage performs an integer multiply, as illustrated at 32. The purpose of the multiplication is to combine the incoming correction integer value with the locally provided value so that a single integer correction value may be output. This multiplication is also required by any subsequent processing stages (not shown) which provide any additional correction values which may be required.

FIG. 3 illustrates a circuit representation for on-line weighted histogramming. A real-time LOR information packet including the respective bin address and normalizing integer value is input to a latch 38. This information is latched and then applied to the RAM array 40. The RAM array 40 contains the projection space bins undergoing the histogramming process. As each LOR packet arrives, a RAM controller circuit 42 sequences through the following READ/MODIFY/WRITE operation.

1. Read from RAM array 40 the current bin value indexed by the bin address.
2. Apply the bin value produced by the RAM array 40 together with the normalization value for this LOR packet to the adder circuit 44.
3. Write the output of the adder circuit 44 to the same bin address used in 1.

At the end of the data acquisition, the completed projection data set in the RAM array 40 is read and output for further processing.

From the foregoing description, it will be recognized by those skilled in the art that a device for on-line correction of patient motion in 3D PET offering advantages over the prior art has been provided. Specifically, the device is designed to apply a correction for patient motion in an on-line and real-time manner. The device provides a means whereby as each PET coincidence event is detected, each line of response (LOR) is re-mapped or rebinned in real time from a stationary 3-D reference space of the PET detector array into a virtual 3-D reference space which moves dynamically with the patient. The de-blurring of the PET data is accomplished through the combination of 3-D translation, normalization and weighted histogramming.

While a preferred embodiment has been shown and described, it will be understood that it is not intended to limit the disclosure, but rather it is intended to cover all modifications and alternate methods falling within the spirit and the scope of the invention as defined in the appended claims.

Having thus described the aforementioned invention, I claim:

1. A device for on-line correction of patient motion in three-dimensional positron emission tomography wherein a positron emission tomograph device is used to collect coincidence event and position data, said device comprising:
   a first digital pipeline latch for receiving said data collected by said positron emission tomograph device;
   a plurality of multipliers disposed in parallel, each of said plurality of multipliers for receiving and multiplying a portion of said data to generate a product simultaneous with each other of said plurality of multipliers;
   a second digital pipeline latch for simultaneously receiving said product from each of said plurality of multipliers;
   a plurality of adders disposed in parallel, each of said plurality of adders for receiving and summing a plurality of said product from said plurality of multipliers; and
   a third digital pipeline latch for receiving data from said plurality of adders, said data being representative of a pair of transformed coordinate points from a primary coordinate system to a secondary coordinate system;
   wherein said plurality of multipliers and said plurality of adders are provided to produce transformed coordinates from said primary coordinate system to said secondary coordinate system for each of a pair of detectors using the equations:

$$x_a' = d_{xx}*x_a + d_{xy}*y_a + d_{xz}*z_a + X; \quad (1)$$

$$y_a' = d_{yx}*x_a + d_{yy}*y_a + d_{yz}*z_a + Y; \quad (2)$$

$$z_a' = d_{zx}*x_a + d_{zy}*y_a + d_{zz}*z_a + Z; \quad (3)$$

$$x_b' = d_{xx}*x_b + d_{xy}*y_b + d_{xz}*z_b + X; \quad (4)$$

$$y_b' = d_{yx}*x_b + d_{yy}*y_b + d_{yz}*z_b + Y; \text{ and} \quad (5)$$

$$z_b' = d_{zx}*x_b + d_{zy}*y_b + d_{zz}*z_b + Z; \quad (6)$$

where:
   X, Y, and Z are translational offsets from a point (x, y, z) in said primary coordinate system to a point (x', y', z') in said secondary coordinate system;
   $d_{xx}$, $d_{xy}$, and $d_{xz}$ are direction cosines between the x-, y-, and z-axes and the x' axis, respectively;
   $d_{yx}$, $d_{yy}$, and $d_{yz}$ are direction cosines between the x-, y-, and z-axes and the y' axis, respectively;
   $d_{zx}$, $d_{zy}$, and $d_{zz}$ are direction cosines between the x-, y-, and z-axes and the z' axis, respectively; and
   a and b are two detectors in a detector pair;
   whereby as said data is input to said first digital pipeline latch, said product of said data from an immediately previous said event is input to said second digital pipeline latch and completely transformed data from a second immediately previous said data is input to said third digital pipeline latch, and whereby said event data is transformed from said primary coordinate system to said secondary coordinate system in real time.

2. The device of claim 1 wherein said plurality of multipliers includes eighteen said multipliers, one each being provided to multiply one ordinate of one of said detector pair in said primary coordinate system with one said direction cosine as set forth in equations (1) through (6), and wherein said plurality of adders includes six said adders, one each being provided to sum three said products from said plurality of multipliers and one said translational offset as set forth in equations (1) through (6), whereby said transformed coordinates (x', y', z') for each of said pair of detectors are acquired.

3. A method for on-line correction of patient motion in three-dimensional positron emission tomography wherein a positron emission tomograph device is used to collect coincidence event data, said method comprising the steps of:
   a) collecting data relative to a scan;
   b) delivering said scan data to a processor having a first digital pipeline latch, a plurality of multipliers, a second digital pipeline latch, a plurality of adders, and a third digital pipeline latch;
   c) multiplying selected groups of said data in said plurality of multipliers to simultaneously acquire a plurality products;
   d) delivering said plurality of products to said second digital pipeline latch;
   e) summing a selected group of said plurality of products in said plurality of adders to acquire a plurality of sums representative of transformed coordinates from a primary coordinate system to a secondary coordinate system, wherein said plurality of multipliers and said plurality of adders are provided to produce transformed coordinates from said primary coordinate system to said secondary coordinate system for each of a pair of detectors using the equations:

$$x_a' = d_{xx}*x_a + d_{xy}*y_a + d_{xz}*z_a + X; \quad (1)$$

$$y_a' = d_{yx}*x_a + d_{yy}*y_a + d_{yz}*z_a + Y; \quad (2)$$

$$z_a' = d_{zx}*x_a + d_{zy}*y_a + d_{zz}*z_a + Z; \quad (3)$$

$$x_b' = d_{xx}*x_b + d_{xy}*y_b + d_{xz}*z_b + X; \quad (4)$$

$$y_b' = d_{yx}*x_b + d_{yy}*y_b + d_{yz}*z_b + Y; \text{ and} \quad (5)$$

$$z_b' = d_{zx}*x_b + d_{zy}*y_b + d_{zz}*z_b + Z; \quad (6)$$

where:
X, Y, and Z are translational offsets from a point (x, y, z) in said primary coordinate system to a point (x', y', z') in said secondary coordinate system;

$d_{xx}$, $d_{xy}$, and $d_{xz}$ are direction cosines between the x-, y-, and z-axes and the x' axis, respectively;

$d_{yx}$, $d_{yy}$, and $d_{yz}$ are direction cosines between the x-, y-, and z-axes and the y' axis, respectively;

$d_{zx}$, $d_{zy}$, and $d_{zz}$ are direction cosines between the x-, y-, and z-axes and the z' axis, respectively; and a and b are two detectors in a detector pair;

f) delivering said plurality of sums to said third digital pipeline latch.

4. The method of claim 3 wherein said plurality of multipliers includes eighteen said multipliers, one each being provided to multiply one ordinate of one of said detector pair in said primary coordinate system with one said direction cosine as set forth in equations (1) through (6), and wherein said plurality of adders includes six said adders, one each being provided to sum three said products from said plurality of multipliers and one said translational offset as set forth in equations (1) through (6), whereby said transformed coordinates (x', y', z') for each of said pair of detectors are acquired.

5. A method for on-line correction of patient motion in three-dimensional positron emission tomography wherein a positron emission tomograph device is used to collect coincidence event data, said method comprising the steps of:
   a) collecting data relative to a scan;
   b) delivering said scan data to a processor having a first digital pipeline latch, a plurality of multipliers, a second digital pipeline latch, a plurality of adders, and a third digital pipeline latch;
   c) normalizing said data comprising the steps of:
      1) inputting event data into a first normalizing pipeline latch to provide a transaxial geometric correction value for said event;
      2) providing a geometric correction value for said event;
      3) inputting said geometric correction value and information regarding said event to a second normalizing pipeline latch;
      4) providing a dead time correction value for said event; and
      5) performing an integer multiply of said geometric correction value and said dead time correction value;
   d) multiplying selected groups of said data in said plurality of multipliers to simultaneously acquire a plurality products;
   e) delivering said plurality of products to said second digital pipeline latch;
   f) summing a selected group of said plurality of products in said plurality of adders to acquire a plurality of sums representative of transformed coordinates from a primary coordinate system to a secondary coordinate system; and
   g) delivering said plurality of sums to said third digital pipeline latch.

6. A method for on-line correction of patient motion in three-dimensional positron emission tomography wherein a positron emission tomograph device is used to collect coincidence event data, said method comprising the steps of:
   a) collecting data relative to a scan;
   b) delivering said scan data to a processor having a first digital pipeline latch, a plurality of multipliers, a second digital pipeline latch, a plurality of adders, and a third digital pipeline latch;
   c) normalizing said data;
   d) histogramming said data including the steps of:
      1) reading from a memory a current bin value indexed by a bin address;
      2) applying said bin value produced by said memory together with a normalization value for said current bin to an adder; and
      3) writing an output of said adder to said current bin
   d) multiplying selected groups of said data in said plurality of multipliers to simultaneously acquire a plurality products;
   e) delivering said plurality of products to said second digital pipeline latch;
   f) summing a selected group of said plurality of products in said plurality of adders to acquire a plurality of sums representative of transformed coordinates from a primary coordinate system to a secondary coordinate system; and
   g) delivering said plurality of sums to said third digital pipeline latch.

7. A method for on-line correction of patient motion in three-dimensional positron emission tomography wherein a positron emission tomograph device is used to collect coincidence event data, said method comprising the steps of:
   a) collecting data relative to a scan;
   b) delivering said scan data to a processor having a first digital pipeline latch, a plurality of multipliers, a second digital pipeline latch, a plurality of adders, and a third digital pipeline latch;
   c) normalizing said data;
   d) histogramming said data;
   e) multiplying selected groups of said data in said plurality of multipliers to simultaneously acquire a plurality products;
   f) delivering said plurality of products to said second digital pipeline latch;
   g) summing a selected group of said plurality of products in said plurality of adders to acquire a plurality of sums representative of transformed coordinates from a primary coordinate system to a secondary coordinate system; and
   h) delivering said plurality of sums to said third digital pipeline latch.

* * * * *